United States Patent
Muir et al.

(10) Patent No.: US 10,724,098 B2
(45) Date of Patent: Jul. 28, 2020

(54) METHOD TO PREDICT LIKELIHOOD OF INHERITED PERIPHERAL NEUROPATHY IN MAMMALS

(71) Applicant: Wisconsin Alumni Research Foundation, Madison, WI (US)

(72) Inventors: Peter Muir, Madison, WI (US); Susannah Sample, Madison, WI (US); John Svaren, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/599,730

(22) Filed: May 19, 2017

(65) Prior Publication Data

US 2017/0335398 A1 Nov. 23, 2017

Related U.S. Application Data

(60) Provisional application No. 62/338,773, filed on May 19, 2016.

(51) Int. Cl.
| | | |
|---|---|---|
| *C12Q 1/68* | (2018.01) | |
| *C07H 21/04* | (2006.01) | |
| *C12Q 1/6883* | (2018.01) | |
| *A01K 67/02* | (2006.01) | |

(52) U.S. Cl.
CPC ............ *C12Q 1/6883* (2013.01); *A01K 67/02* (2013.01); *C12Q 2600/106* (2013.01); *C12Q 2600/118* (2013.01); *C12Q 2600/124* (2013.01); *C12Q 2600/156* (2013.01)

(58) Field of Classification Search
None
See application file for complete search history.

(56) References Cited

U.S. PATENT DOCUMENTS

2013/0263294 A1* 10/2013 Martinez .............. C12Q 1/6883
800/8

OTHER PUBLICATIONS

Tacher et al. (J. of Heredity, vol. 96, No. 7, pp. 812-816, 2005) (Year: 2005).*
Tiira et al. (PLoS ONE, vol. 7, No. 7, e41684, Jul. 2012 (Year: 2012).*
Safra et al. (Veterinary Journal, vol. 189, pp. 220-226, 2011 (Year: 2011).*
Ekenstedt et al. (PLOS Genetics, vol. 10, No. 10, p. e1004635, Oct. 2014) (Year: 2014).*

* cited by examiner

*Primary Examiner* — Jeanine A Goldberg
(74) *Attorney, Agent, or Firm* — Joseph T. Leone, Esq.; Dewitt LLP

(57) ABSTRACT

Methods and kits for diagnosing propensity to exhibit acquired peripheral neuropathy in dogs are described. The methods and kits test dogs for presence of a single-nucleotide polymorphism (SNP) TIGRP2P18586_rs8746233. Presence of the SNP indicates an increased likelihood of the dog exhibiting an acquired peripheral neuropathy. This information can be used to guide preemptive clinical treatment of the animal for peripheral neuropathy and to choose dogs for selective breeding programs.

2 Claims, 2 Drawing Sheets

METHOD TO PREDICT LIKELIHOOD OF INHERITED PERIPHERAL NEUROPATHY IN MAMMALS

CROSS-REFERENCE TO RELATED APPLICATIONS

Priority is hereby claimed to provisional application Ser. No. 62/338,773, filed May 19, 2016, which is incorporated herein by reference.

BACKGROUND

Peripheral neuropathies are a heterogeneous group of diseases that cause pathologic degeneration of the peripheral nervous system, and may involve motor, sensory and autonomic fiber types. Damage to peripheral nerves has several etiologies, including systemic disease such as diabetes and hypothyroidism, toxin exposures, nutritional deficiencies, infections and hereditary disorders. Neuropathy is also a feature of the aging process.

The most common inherited peripheral neuropathy in humans, Charcot-Marie-Tooth (CMT) disease, causes progressive deterioration of motor and sensory nerves, muscular atrophy, and chronic pain. About 1 in 2,500 individuals are affected by CMT. Current treatments for CMT manage symptoms rather than modify the disease course. CMT results in axonal degeneration in nerves with long axons, such that the neuropathy is generally more pronounced distally. Differentiation of various neuropathies is dependent on patient history, exclusion of metabolic disease, electro-diagnostics and genetic testing. In humans, CMT variants include CMT type 1 (CMT1) and CMT type 2 (CMT2). CMT1 variants are de- or dysmyelinating, while CMT2 variants are axonal neuropathies. In humans, over 80 causative genetic variants associate with CMT, although the genetic cause for many cases remains unknown. CMT1 is associated with mutations in genes that encode proteins influencing Schwann cell function and myelination. CMT2-associated genes are associated with critical axonal processes such as mitochondrial dynamics.

Idiopathic acquired laryngeal paralysis in the dog was first identified in the mid-1950s. (O'Brien J A, Harvey C E, Kelly A M, Tucker J A. Neurogenic atrophy of the laryngeal muscles of the dog. J Small Anim Pract 1973; 14(9):521-32.) Today it is a well-recognized specific clinical syndrome confirmed as a generalized acquired peripheral neuropathy (APN) condition with high prevalence in specific dog breeds. Clinically and diagnostically, APN resembles human CMT disease with associated alterations in electro-diagnostic profiles and pathologic changes to peripheral nerves. Although rare, CMT disease symptoms in humans can include laryngeal paralysis. Many canine diseases are caused by mutations in the same genes that produce corresponding disease in humans, including complex traits, such as hip dysplasia, and monogenic traits, such as muscular dystrophy.

Thus, for example, a major barrier to rapid progress in the development of disease-modifying medical treatment for human patients affected with peripheral neuropathy is a lack of understanding of the genetic basis of the disease and the lack of suitable large animal models. Continued existence of this barrier represents an important problem because, currently, therapies for patients with peripheral neuropathy and other types of motor neuron disease such as amyotrophic lateral sclerosis (ALS) and CMT are entirely symptomatic and do not modify or reverse progression of the disease over time.

In certain dog breeds, acquired peripheral neuropathy (APN) syndrome is common. Labrador Retrievers represent >70% of APN cases, although other breeds can also be affected, particularly Golden Retrievers, Poodles, and Irish Setters. It is estimated that as many as 50-75% of Labrador Retrievers get APN when over 12 years of age. The Labrador Retriever is the most common dog breed in the USA. Affected dogs have often been used for breeding before clinical signs develop. There is currently no disease modifying therapy available for dogs with APN. Moreover, presentation of APN in the dog is similar to both ALS and CMT diseases in humans. Humans with CMT can develop upper airway disorders, and fast-course ALS patients may present with laryngeal paralysis. Thus, there is a long-felt and unmet need for a diagnostic test that predicts the likelihood that a mammalian subject will exhibit, as some point in its life, an acquired peripheral neuropathy.

DETAILED DESCRIPTION

Abbreviations and Definitions

Figure 1:
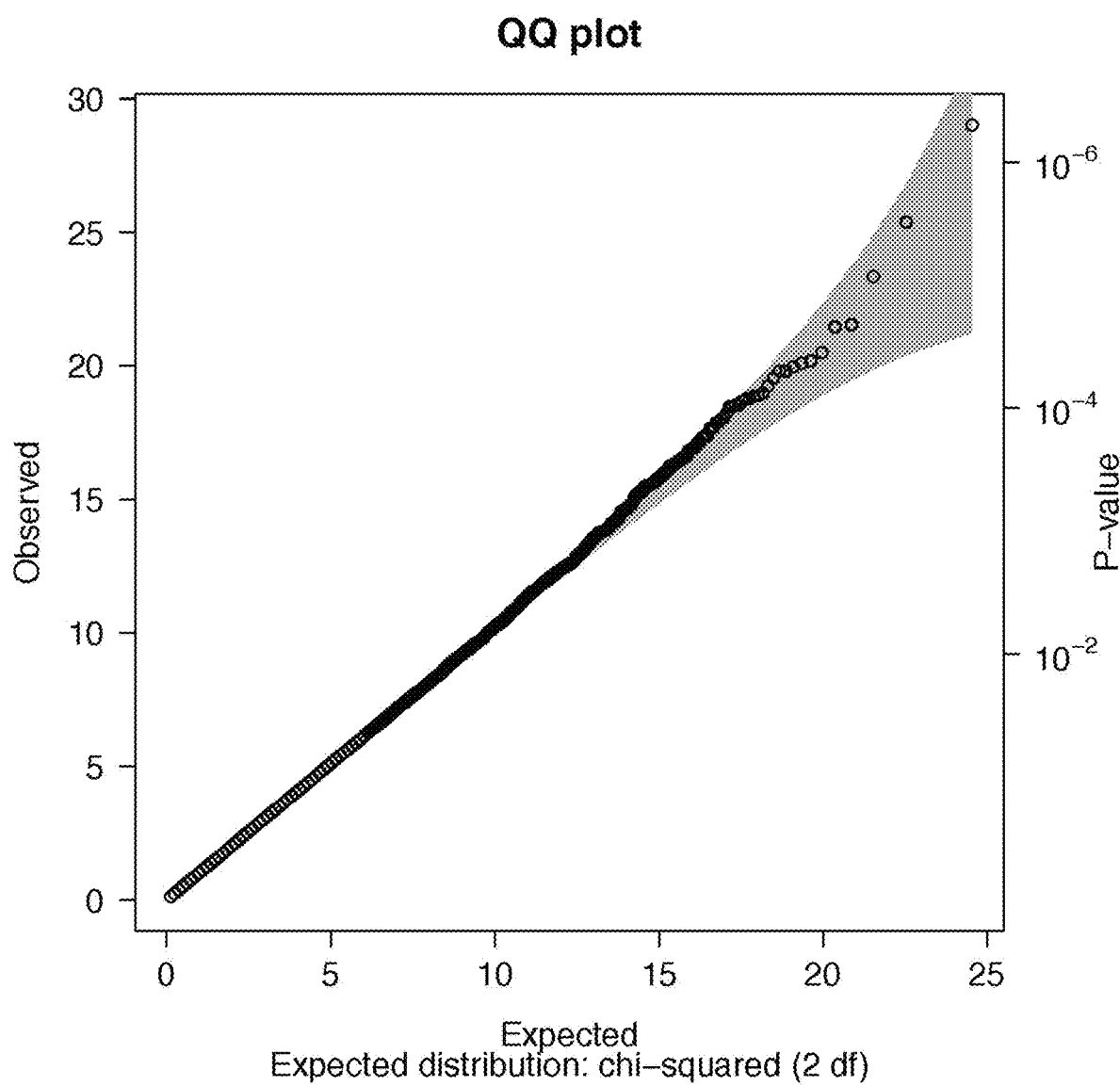
FIG. 1 is a quantile-quantile (QQ) plot of data from a genome-wide association study of Labrador Retriever dogs exhibiting acquired peripheral neuropathy (APN). Values on the Y-axis represent the negative log of the uncorrected p-value for SNP association with APN. The QQ plot suggests genomic inflation is corrected by the linear mixed model, as the SNP P-values follow the confidence interval other than the SNP with a low P values. Lambda=1.02. The SNP on CFA1 was associated with APN at P=5.00E-7. This SNP is near numerous candidate genes associated with neuronal regulation. Data are derived from 56 cases and 26 controls using the Illumina CanineHD Genotyping BeadChip (Illumina, Inc., San Diego, Calif., USA).

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made. Unless otherwise stated, the indefinite articles "a" and "an" mean "one or more." When referring to a previously stated element, the definite article "the" does not limit the stated definition of "a" and "an," as meaning "one or more."

All combinations of method or process steps as used herein can be performed in any order, unless otherwise specified or clearly implied to the contrary by the context in which the referenced combination is made.

The methods and kits disclosed herein can comprise, consist of, or consist essentially of the essential elements and limitations described herein, as well as any additional or optional steps, ingredients, components, or limitations described herein or otherwise useful in gathering, preparing, and sequencing genomic DNA for analysis.

GEMMA: Genome-wide efficient mixed model association. GEMMA is a free, open-source whole genome association analysis program that performs a range of large-scale genomic analyses in a computationally efficient manner. It is available online from the website of Professor Xiang Zhou of the University of Michigan, School of Public Health, Department of Biostatistics School of Public Health, Ann Arbor, Mich. See http://www.xzlab.org/software.html. GEMMA is the software used to implement the Genome-wide Efficient Mixed Model Association algorithm for a standard linear mixed model and some of its close relatives for genome-wide association studies (GWAS). It fits a univariate linear mixed model (LMM) for marker association tests with a single phenotype to account for population stratification and sample structure, and for estimating the proportion of variance in phenotypes explained (PVE) by typed genotypes ("chip heritability"). It fits a multivariate linear mixed model (mvLMM) for testing marker associations with multiple phenotypes simultaneously while controlling for population stratification, and for estimating genetic correlations among complex phenotypes. It fits a Bayesian sparse linear mixed model (BSLMM) using Markov chain Monte Carlo (MCMC) for estimating PVE by typed genotypes, predicting phenotypes, and identifying associated markers by jointly modeling all markers while controlling for population structure. It estimates variance component/chip heritability, and partitions it by different SNP functional categories. In particular, it uses a Haseman Elston regression or restricted maximum likelihood (REML) artificial intelligence algorithm to estimate variance components when individual-level data are available. It is computationally efficient for large scale GWAS and uses freely available open-source numerical libraries. It is distributed under the GNU General Public License. See Xiang Zhou and Matthew Stephens (2012) "Genome-wide efficient mixed-model analysis for association studies," *Nature Genetics* 44: 821-824; Xiang Zhou and Matthew Stephens (2014) "Efficient multivariate linear mixed model algorithms for genome-wide association studies," *Nature Methods* 11(4): 407-409; Xiang Zhou, Peter Carbonetto and Matthew Stephens (2013) "Polygenic modeling with Bayesian sparse linear mixed models," *PLoS Genetics* 9(2): e1003264; and Xiang Zhou (2016) "A unified framework for variance component estimation with summary statistics in genome-wide association studies," *bioRxiv*. 042846 (http://biorxiv.org/content/early/2016/03/08/042846; a preprint server hosted by the Cold Spring Harbor Laboratory, Cold Spring Harbor, N.Y.).

GWAS: Genome-wide association study. A genome-wide association study is an analysis of genetic variation at specified loci in different individuals to see if any variant(s) is (are) associated with a phenotypic trait. As the name indicates, genetic markers across the complete genome of each individual test subject are tested to find genetic variations associated with a particular disease, in this case APN in dogs. Once new genetic associations are identified, the information is used to detect, treat and/or prevent the disease. Such studies are particularly useful in finding genetic variations that contribute to common, but complex diseases.

LD: Linkage disequilibrium. Linkage disequilibrium is the non-random association of alleles at two or more loci that descend from single, ancestral chromosomes.

MDS: multidimensional scaling.

MLM, LLM (synonymous): mixed linear model, linear mixed model, respectively.

PLINK: PLINK is a free, open-source whole genome association analysis program that performs a range of large-scale genomic analyses in a computationally efficient manner. The PLINK software was developed (and continues to be refined) by Shaun Purcell, Christopher Chang, and others at the Center for Human Genetic Research, Massachusetts General Hospital, and the Broad Institute of Harvard and M.I.T., as well as Stanford University's Department of Biomedical Data Science. PLINK v.1.9 is available online as of May 19, 2017 at https://www.cog-genomics.org/plink/1.9/. Plink v. 2.0 was released May 9, 2017, and is available online at https://www.cog-genomics.org/plink/2.0/. See Christopher C Chang, Carson C Chow, Laurent C A M Tellier, Shashaank Vattikuti, Shaun M Purcell and James J Lee (2015) "Second-generation PLINK: rising to the challenge of larger and richer datasets," *GigaScience* 4:7 (DOI: 10.1186/s13742-015-0047-8) and Shaun Purcell, Benjamin Neale, Kathe Todd-Brown, Lori Thomas, Manuel A. R. Ferreira, David Bender, Julian Maller, Pamela Sklar, Paul I. W. de Bakker, Mark J. Daly, and Pak C. Sham (2007) "PLINK: A Tool Set for Whole-Genome Association and Population-Based Linkage Analyses," *Am J Hum Genet.* 81(3): 559-575 (published online Jul. 25, 2007 (DOI: 10.1086/519795).

SNP: Single nucleotide polymorphism.

Unless otherwise noted, technical terms are used according to conventional usage. Definitions of common terms in genetics, genomics, and molecular biology may be found in Benjamin Lewin, "Genes V," published by Oxford University Press, 1994 (ISBN 0-19-854287-9) and Kendrew et al. (eds.), "The Encyclopedia of Molecular Biology," published by Blackwell Science Ltd., 1994 (ISBN 0-632-02182-9).

Genome-Wide Association Study

Figure 2:
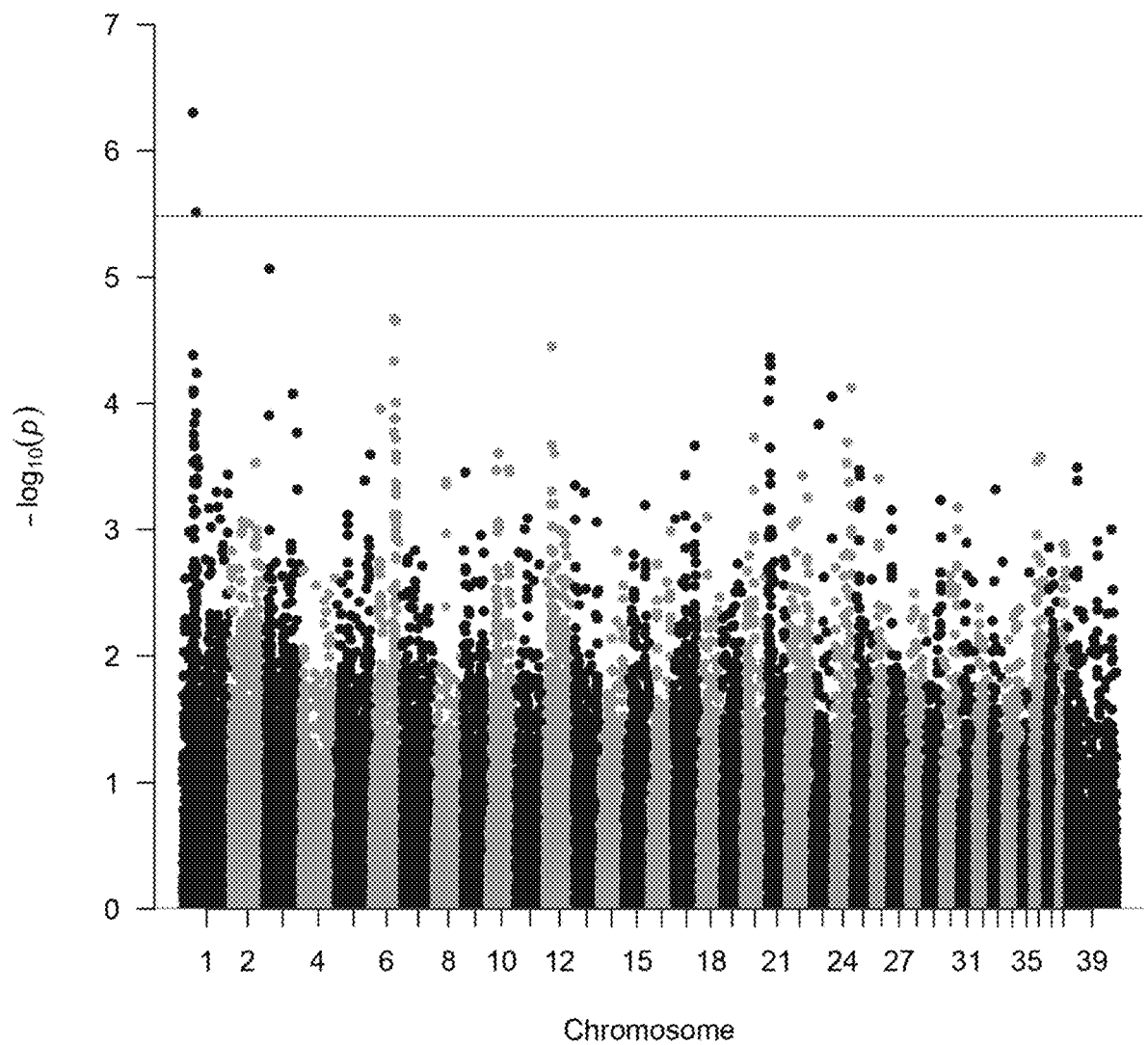
FIG. 2 is a Manhattan plot of the data presented in FIG. 1. The X-axis displays the genomic coordinates by chromosome number. The Y-axis displays the negative logarithm of the association P-value for each single nucleotide polymorphism (SNP) displayed on the Y-axis; each dot on the Manhattan plot signifies a SNP. Because the strongest associations have the smallest P values (e.g., $10^{-5}$), their negative logarithms have the greatest values (e.g., 5) on the Y-axis in the corresponding Manhattan plot.

We have conducted a genome-wide association study using a population of Labrador Retrievers consisting of 56 cases and 26 controls. This study shows that a single nucleotide polymorphism (SNP) on CFA1 tags the causal variant for APN in mammals generally, dogs particularly, and Labrador Retrievers most specifically. This SNP (TIGRP2P18586_rs8746233) is located at 29193391 on CFA1, is associated with APN (P=5.00E-7) and is located in a region of numerous genes associated with neuronal regulation. Permutation testing indicates that this P value meets genome-wide significance. The SNP is not in strong linkage disequilibrium with any other SNP on the Illumina SNP Array, indicating that the causal variant lies within a 16 Mb interval, between 24 Mb and 40 Mb on CanFam2.1). See FIGS. 1 and 2 The GWAS was done using a linear mixed model with GEMMA that accounts for population stratification. Genomic-wide significance was calculated from the 5% quantile of the population of minimum P values from 10,000 GWAS permutations with randomly permuted phenotypes.

Importantly, model-based tests suggest that the associated SNP on CFA1, which is a marker for the causal variant, is inherited in an autosomal dominant fashion in the Labrador Retriever, as is the case with familial ALS and many forms of CMT in people. See Table 1.

TABLE 1

|  | GG | GA | AA |
|---|---|---|---|
| Case | 15 | 30 | 11 |
| Control | 0 | 5 | 21 |

In Labrador Retrievers, the major allele for this SNP is G and the minor allele is A. The GG genotype indicates that even SNP-based genetic testing of Labrador Retrievers has commercial value in the veterinary market for genetic testing for selective breeding and preemptive clinical management of affected dogs.

Canine Samples and Phenotyping

DNA was isolated from client-owned Labrador Retrievers using blood or buccal swabs. A four-generation pedigree was collected from each dog to ensure purebred status and identify siblings, which were excluded from the GWAS.

Genome-Wide Association

Genome-wide SNP genotyping was performed in 56 cases and 26 controls using the Illumina CanineHD BeadChip, which genotypes 173,662 SNPs evenly spaced across the genome. Data underwent quality control filtering using PLINK [Chang C C, Chow C C, Tellier L C A M, Vattikuti S, Purcell S M, Lee J J. Second-generation PLINK: rising to the challenge of larger and richer datasets. GigaScience. 2015; 4:7]. All samples had a genotyping call rate of ≥95%. SNPs were excluded if the minor allele frequency (MAF) was ≤0.05; SNPs were also excluded if the genotyping rate was ≤95%). SNPs were also excluded if they deviated from Hardy-Weinberg equilibrium at P<1E-07.

To account for ancestral population structure and family relatedness in the study dogs, single marker linear mixed model (LMM) analysis was performed using GEMMA (Genome-wide Efficient Mixed Model Association) [Zhou X, Stephens M. Genome-wide efficient mixed-model analysis for association studies. Nat Genet. 2012; 44: 821-824], a software tool optimized for complex trait GWAS.

To further assess the genetic architecture that explains APN, we will undertake GWAS using a Bayesian mixture model (BayesR) in which all of the SNPs are fitted simultaneously in the model to enable SNP trait associations, estimation of heritability, and analysis of the genetic architecture of the disease through partitioning of variance across hundreds or thousands of SNPs (Moser G, Lee S H, Jayes B J, et al. Simultaneous discovery, estimation, and prediction analysis of complex traits using a Bayesian mixture model. PLoS Genetics 2015; 11:e1004969). This approach is novel relative to the traditional use of single-SNP analysis or a linear mixed model for GWAS. We will also assess the proportion of additive genetic variance contributed by individual chromosomes and the proportion of variance on each chromosome explained by SNPs with different effect sizes.

Genome-Wide Significance

We defined genome-wide significance using permutation testing. Use of a Bonferroni correction for the number of SNPs tested is too conservative in dog breeds, as extensive LD means that SNPs are often inherited in haplotype blocks [Lindblad-Toh K, Wade C M, Mikkelsen T S, Karlsson E K, Jaffe D B, Kamal M, et al. Genome sequence, comparative analysis, and haplotype structure of the domestic dog. Nature. 2005; 438: 803-819]. We will define genome-wide significance by randomly permuting the phenotypes and re-running the GWAS LMM 10,000 times. Genome-wide significance was defined by identifying the 5% quantile of the set of minimum P-values from the GWAS permutations. Additionally, we calculated the number of haplotype blocks in the Labrador Retriever SNP data using PLINK, using LD windows of 500 kb, 1 Mb, and 5 Mb and used the number of haplotype blocks to estimate genome-wide significance by Bonferroni correction of P<0.05.

Defining Associated Loci in the Genome

After obtaining the results from the GEMMA LMM for the APN trait, LD-based clumping was calculated in PLINK to define the region of association with the APN trait from the GWAS results. LD clumping defined a candidate locus around the associated SNP. A region within ($r^2$>0.5, within 2 Mb of the associated SNP) was defined. These settings were modified from another GWAS for a complex trait in dogs. [Karlsson et al. (2013). Genome-wide analyses implicate 33 loci in heritable dog osteosarcoma, including regulatory variants near CDKN2A/B. *Genome Biology*. 14:R132.] These regions were then investigated with the NCBI Canine Genome Map Viewer to identify nearby genes using the CanFam 3.0 reference sequence.

Mode of Inheritance

Model-based analysis of case and control genotypes was performed using PLINK. This suggested that the associated SNP on CFA1, which is a marker for the causal variant, is inherited in an autosomal dominant fashion in the Labrador Retriever, as is the case with familial ALS and many forms of CMT in people. In addition, a more detailed pedigree tree is being constructed using four-generation pedigrees from each dog to evaluate the mode of inheritance.

Fine Mapping

Fine mapping should include the original GWAS breed and use of another breed sharing the phenotype, as haplotypes are commonly shared between breeds. A replicated/validated risk loci GWAS data set will be generated using Labrador and Golden Retriever SNPs. Fine-mapping association analysis will include a between-breed association design using both breeds (Karlsson & Lindblad-Toh 2008). Fine mapping will use the KASP™—brand genotyping (LGC Genomics, Beverly, Mass.) and a dense set of SNPs selected from breed-specific whole genome sequences Low-Density Whole-Genome Sequencing DNA will be isolated from a blood sample or a saliva swab. dsDNA purity and concentration will be assessed. DNA from selected dogs will be submitted to the University of Wisconsin-Madison Biotechnology Center. DNA concentration will be verified using the Qubit® dsDNA HS Assay Kit (Life Technologies, Grand Island, N.Y.). 1 ug of each sample will be sheared using a Covaris M220 Ultrasonicator (Covaris Inc, Woburn, Mass.) to an average insert size of 550 bp, and sizing will be verified by Fragment Analyzer (Advanced Analytical Technologies, Inc., Ames, Iowa). Libraries will be prepared according the NEB Next®

Ultra™ DNA Library Prep Kit for Illumina (New England Biolabs, Ipswich, Mass.) with minor modifications. Quality and quantity of the finished libraries will be assessed using the Fragment Analyzer and Qubit® dsDNA HS Assay Kit, respectively. Libraries will be standardized to 2 µM. Cluster generation will be performed using HiSeq PE Cluster Kit v3 cBot kits (Illumina Inc, San Diego, Calif.). Flowcells will be sequenced using paired-end, 100 bp sequencing and HiSeq SBS Kit v3 (200 Cycle) (Illumina Inc.) on a HiSeq2500 sequencer, to a depth of 5.6-8.5× per library. Images will be analyzed using the standard Illumina Pipeline.

Variant Filtering:

The resulting 100-base paired-end sequences will be mapped to the genome (CanFam3.1). Single nucleotide polymorphisms (SNPs) from dogs with both Canine HD Genotyping BeadChip (Illumina Inc, San Diego, Calif.) data and whole-genome sequencing data will be compared to assure the resulting genotypes are identical. All SNPs identified by the whole-genome sequencing data will subsequently be filtered for low genotype quality scores. An association analysis will be performed using PLINK with options specifying an additive model. The conservative Bonferroni correction method will be used to correct for multiple testing.

Structural Variant Analysis:

We will utilize the DELLY program (Rausch T, Zichner T, Schlattl A, Stutz A M, Benes V, Korbel J O. DELLY: structural variant discovery by integrated paired-end and split-read analysis. Bioinformatics 2012; 28:i333-9) to evaluate the whole-genome sequence data for genomic structural variants that associate with disease phenotype in our region of interest. Variants including deletions, duplications, inversions and translocations will be accessed between cases and controls for Labrador and Golden Retrievers.

What is claimed is:

1. A method for breeding a dog, the method comprising:
   (a) isolating genomic DNA from a first dog
   (b) assaying the genomic DNA of step (a) for presence of a single-nucleotide polymorphism (SNP) TIGRP2P18586_rs8746233;
   (c) detecting an A allele at TIGRP2P18586_rs8746233 in the genomic DNA of step (b);
   (d) selecting a first dog with an A at TIGRP2P18586_rs8746233 and then
   (e) breeding the first dog having an "A" allele at TIGRP2P18586_rs8746233.

2. The method of claim 1, wherein step (b) comprises:
   (i) contacting the genomic DNA with at least one oligonucleotide probe dimensioned and configured to bind selectively to the SNP TIGRP2P18586_rs8746233; and then
   (ii) detecting whether any portion of the genomic DNA of the dog selectively binds to the oligonucleotide probe, wherein binding indicates presence of the SNP in the genomic DNA of the dog.

* * * * *